United States Patent

Unruh et al.

Patent Number: 5,367,106
Date of Patent: Nov. 22, 1994

[54] COUPLED SECONDARY OXO REACTION SYSTEM

[75] Inventors: Jerry D. Unruh, Corpus Christi; Wendell L. Pieper, Portland; Milo C. Pass, Corpus Christi, all of Tex.

[73] Assignee: Hoechst Celanese Corporation, Somerville, N.J.

[21] Appl. No.: 123,075

[22] Filed: Sep. 20, 1993

[51] Int. Cl.⁵ .............................................. C07C 45/50
[52] U.S. Cl. ................................. 568/453; 568/451; 568/452; 568/454
[58] Field of Search ............... 568/454, 451, 452, 453; 556/21

[56] References Cited

U.S. PATENT DOCUMENTS 4,210,426  7/1984  Sridhav ....................... 568/453
5,105,018  4/1992  Miyazawa et al. ............. 568/453

FOREIGN PATENT DOCUMENTS 593954  4/1980  Canada .

Primary Examiner—Werren B. Lone
Attorney, Agent, or Firm—Stuart D. Frenkel; Donald R. Cassady

[57] ABSTRACT

In a primary process for hydroformylating olefins in the presence of a rhodium-containing catalyst solution to produce aldehydes and a gaseous effluent comprising unreacted olefin is vented, the improvement which comprises employing the effluent as a reactant feed for a coupled secondary hydroformylation process conducted jointly therewith in which the catalyst solution is cycled back and forth between the primary and secondary hydroformylation processes.

20 Claims, 1 Drawing Sheet

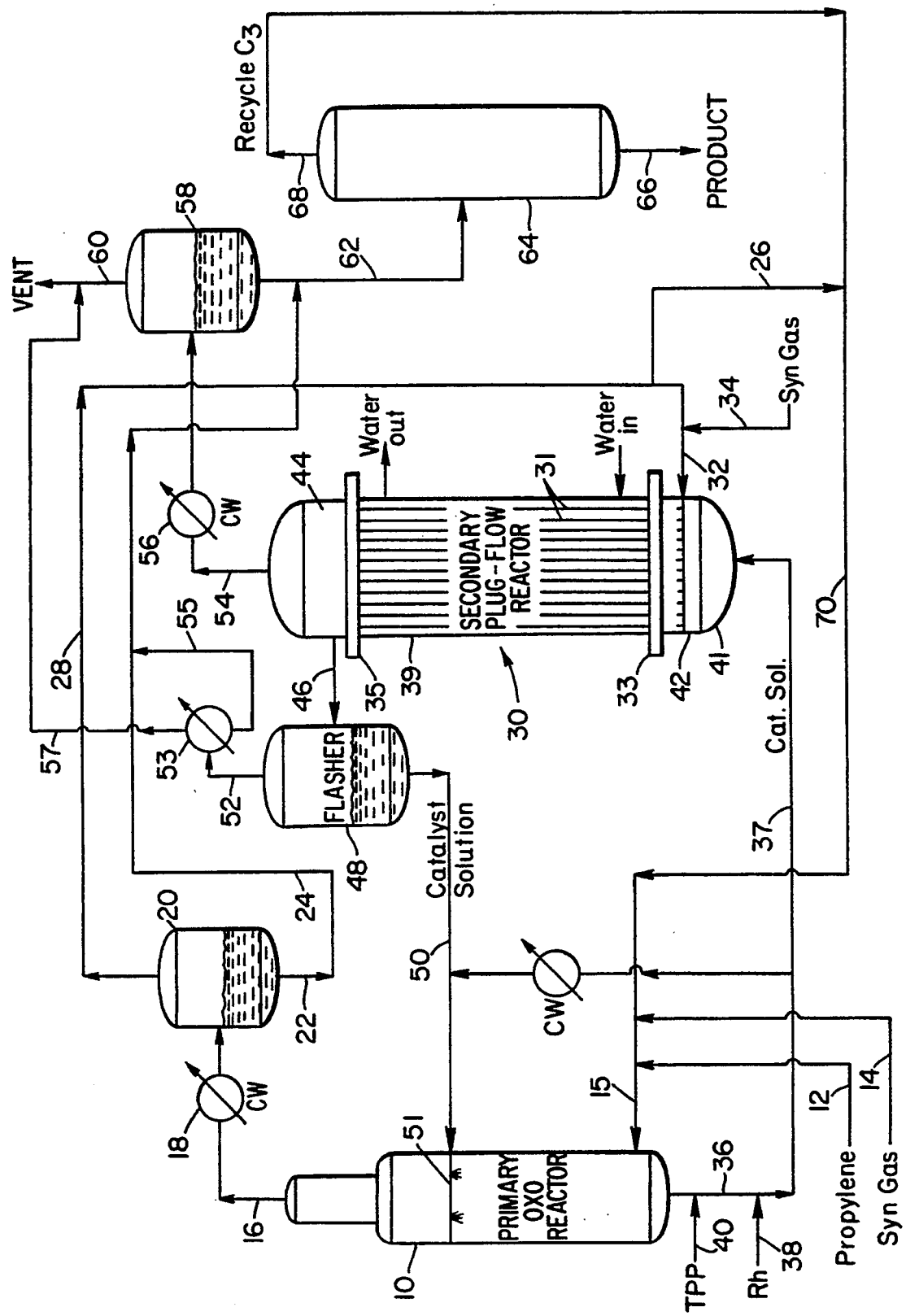

COUPLED SECONDARY OXO REACTION SYSTEM

BACKGROUND OF THE INVENTION

Processes for hydroformylating an olefin to prepare a carbonyl derivative containing one carbon atom more than the parent olefin by reacting the olefin with synthesis gas in the presence of a Group VIII metal, e.g. rhodium, in complex combination with an organic ligand, carbon monoxide also being a component of the catalyst complex, are well known in the art (the "oxo" process) and of growing industrial importance. This technology is summarized, for example, in U.S. Pat. No. 3,527,809 to Pruett et al. The olefin reactant is contacted with the catalyst and the synthesis gas (a mixture of carbon monoxide and hydrogen) in the presence of a liquid reaction medium, which may or may not comprise a separate inert liquid solvent species. The synthesis gas comprising the carbon monoxide and hydrogen is typically bubbled through the liquid reaction medium which is contained in a hydroformylation reactor which can be mechanically stirred or which may be agitated solely by the action of reactant gas being bubbled therethrough. The gas, in addition to hydrogen and carbon monoxide, may also contain vapors of the reactant olefin, in a proportion which will depend upon such factors as reaction conversion rate and the volatility of the olefin.

The aldehyde hydroformylation product can be recovered from the liquid hydroformylation reaction medium in various ways, but, especially when the aldehyde is of comparatively low molecular weight, e.g., when it contains from three to about seven carbon atoms and especially when it contains from three to about five carbon atoms, it is conveniently stripped out in vapor form by distillation, evaporation, or, especially, by being stripped out of the hydroformylation reaction zone in the gases which are being bubbled through the liquid contained therein. Hershman et al have described this technology in "I&EC Product Research and Development" 8, pp 372–375 (1969) in a discussion of hydroformylation of propylene in a gas-sparged reactor.

In more recent years various patents and other publications have appeared directed to the use of special reaction solvents and/or special techniques for stripping the aldehyde product out of the liquid reaction medium. For example, U.S. Pat. No. 4,329,511 issued to Hackman et al describes useful solvents as well as the use of a particular high molecular weight, high-boiling inert liquid reaction solvent in proportions of about 40 to about 95% by weight of the liquid reaction solution for purposes of controlling the rate of stripping at a level such that at a given weight concentration (relatively low) of product aldehyde in the mixture, and the mole fraction of aldehyde in the mixture will be relatively high. The specific solvents used are not considered critical as long as they are: (1) miscible with the catalyst system; (2) miscible with the reactants; (3) miscible with the reaction products; (4) low in volatility so as to facilitate striping reaction product and by-products from it and (5) chemically inert in the hydroformylation reaction system. The disclosed solvents include, for example, alkyl-substituted benzene; pyridine and alkyl-substituted pyridines; tertiary amines; high boiling esters such as dialkyldicarboxylates and triorganophosphates as well as esters of polyols such as trimethylolpropane and pentaerythritol; ketones; alcohols such as butanols; nitriles such as acetronitriles; and hydrocarbons such as kerosene, mineral oil, cyclohexane, naphtha, etc. and aromatics such as biphenyl. The use of polyalkylene glycols such as polyethylene glycol and polypropylene glycol having molecular weights greater than about 700 are stated to be particularly desirable because of their availability and their desirable properties for use as a hydroformylation solvent.

A related hydroformylation process is described in U.S. Pat. No. 4,151,209 to Paul et al, which describes techniques for recovering aldehyde products from the reaction products by distillation, stripping, employing the ratio of phosphorus contained in the high-boiling reaction by-products to the phosphorus contained in the ligand (triorganophophine ligand) which is present, as the primary control. Although the claimed improvement of the Paul et al process is different from that of the process of U.S. Pat. No. 4,239,511, similar solvents have been found to be satisfactory for use in the hydroformylation reactions described in both of these patents.

An alternative catalyst solvent is disclosed in U.S. Pat. No. 4,148,830 issued Apr. 10, 1979 to Pruett et al. As disclosed therein higher boiling aldehyde condensation products are employed as the catalyst solvent. In this patent, liquid effluent from the reaction zone containing catalyst, solvent and gases, is processed to strip and recover the aldehyde product. During this procedure some hydrogen, carbon monoxide, unreacted olefin, and other by-product and inert gases dissolved in the reactor effluent are removed by reducing pressure on the effluent stream to flash off such gases. The desired aldehyde product is then recovered from said effluent and the liquid residue fraction of unrecovered aldehydic product, catalyst and high boiling condensation product is recycled to the reactor. Accordingly, this process has sometimes been referred to as a liquid-recycle hydroformylation process (or "liquid recycle process").

U.S. Pat No. 4,247,486, issued Jan 27, 1981 discloses a hydroformylation process which is directed to further modifications of the basic oxo process disclosed in U.S. Pat. Nos. 3,527,809 and 4,148,830. In this process, unreacted feed, the aldehyde reaction product and higher boiling condensation products, inter alia, are allowed to distill out of the reaction medium such as by being stripped from the reaction medium as previously described. The aldehyde product and condensation products are condensed from the gas stream which contains unreacted feed, (i.e., syn gas and olefin). The gas stream is recycled to the reactor. Moreover, a purge stream comprising gaseous by-product such as propane can be taken from the gas recycle stream to remove such propane and to control its concentration within the process. The purge stream also contains, inter alia, aldehyde product, unreacted olefin inert gases, as well as carbon monoxide and hydrogen. The recovery of olefin from such a stream is impractical and the purge stream is typically used as a fuel.

Likewise, to control total reactor pressure in a liquid recycle process as described above due to build up of inerts and the like, a gaseous purge is generally taken from the liquid recycle hydroformylation reactor, where excess hydrogen, carbon monoxide, unreacted olefin, inerts and alkane by-products, such propane, are vented as off-gas. In addition, during the product separation step in a liquid recycle process, some gases, primarily unreacted olefin and alkane by-product, which remain dissolved in the liquid catalyst-containing effluent, are separated along with the desired aldehyde product. A portion of such separated gases are condensed with the desired aldehyde product. The remaining separated gases can be purged from the system.

The amount of olefin and syn gas components lost by purging in such recycle processes can amount to a significant economic disadvantage over the life of a commercial continuous operation due to the efficiency loss of such purged desirables as unreacted olefin and syn gas.

In German Pat. No. 3,102,281, issued Dec. 23, 1982, a cobalt-catalyzed high pressure hydroformylation of propylene was conducted and the waste gas, resulting from the decobalting of the reaction mix, containing propylene, carbon monoxide and hydrogen, was introduced into a low pressure rhodium catalyzed hydroformylation process, simultaneously conducted. In German Laid-Open Patent No. 3,245,883, published Jun. 14, 1984, flue gas from a low pressure rhodium hydroformylation process containing propylene is compressed and introduced into a high pressure cobalt catalyzed reactor for conversion to aldehyde.

In U.S. Pat. No. 4,593,127 there is disclosed a primary liquid recycle or gas recycle rhodium-catalyzed hydroformylation process for producing aldehydes, wherein an olefin, carbon monoxide and hydrogen are reacted in the presence of a solubilized rhodium-phosphorous complex catalyst, free phosphorus ligand and higher boiling aldehyde condensation by-products to produce an aldehyde product, a gaseous effluent comprising unreacted olefin and any of said aldehyde product, hydrogen, carbon monoxide and an alkane by-product is vented from the process, wherein the improvement comprises conducting a decoupled secondary liquid recycle or gas recycle rhodium-catalyzed hydroformylation process conjointly with the primary process, and the vented gaseous effluent together with make-up carbon monoxide and hydrogen is employed as the reactant feed to the secondary process. The decoupled process of this patent requires its own independent catalyst system and independent product recovery system. A key feature of the invention disclosed therein is that unreacted olefin contained in a vent stream from the primary system can be employed as the sole olefin feed to the decoupled secondary hydroformylation process, i.e. make-up quantities of olefin need not be added to the decoupled hydroformylation process.

SUMMARY OF THE INVENTION

In a primary liquid phase rhodium-catalyzed hydroformylation process for forming aldehydes, wherein an olefin, carbon monoxide and hydrogen are reacted in the presence of a solubilized rhodium-phosphorus complex catalyst and inert solvent to produce aldehyde product and a gaseous effluent comprising unreacted olefin and any of said aldehyde product, hydrogen, carbon monoxide and alkane either by-product or introduced in the feed is vented from the process, the improvement which comprises: conducting a coupled secondary liquid phase rhodium-catalyzed hydroformylation process cojointly with the primary process and the gaseous effluent from the primary process which would otherwise have been vented is employed as the reactant feed to the secondary process. The secondary reaction process utilized to convert the vent stream, in particular, unconverted olefin from the primary reaction process preferably utilizes an efficient plug-flow reactor. Additional synthesis gas, i.e., hydrogen and carbon monoxide are fed to the secondary reactor along with the vent stream to achieve nearly total conversion of the olefin in the vent stream to aldehyde. Make-up quantities of olefin need not be added to the coupled secondary reaction process.

The secondary reactor operates as a coupled system with the primary hydroformylation reactor, utilizing the same catalyst solution therewith. Thus, a portion of the catalyst solution from the primary hydroformylation reactor is circulated through the secondary reactor. After product aldehyde is flashed from the catalyst solution exiting the secondary reactor, the catalyst solution is returned to the primary reactor for further reaction therein. Alternatively, the total catalyst solution including product aldehyde leaving the secondary reactor can be introduced back to the primary reactor for aldehyde product recovery therein.

In the present invention, a hydroformylation process is provided with significant reduced physical losses of valuable compounds, e.g. olefin and syn gas, with enhanced process flexibility and enhanced capacity for product recovery.

The present invention provides for operating two oxo reactors in a "coupled" series mode, with the catalyst solution being continuously cycled between the respective reactors. Product removal can be achieved from the primary reactor alone or separate product removal steps for each reactor can be utilized to provide the stated flexibility. The use of a secondary plug-flow reactor in conjunction with a primary back-mixed reactor in the hydroformylation process is an economical way of achieving high total olefin conversion without employing multiple back-mixed reactors or using large quantities of expensive rhodium catalyst as is the case with U.S. Pat. No. 4,593,127.

BRIEF DESCRIPTION OF THE DRAWING

The Figure is a schematic flow diagram of the hydroformylation process of this invention in which a primary reactor is coupled to a secondary plug-flow reactor

DETAILED DESCRIPTION AND PREFERRED EMBODIMENTS

This invention is applicable to improving any conventional liquid phase rhodium-catalyzed hydroformylation process for producing aldehydes. Such oxo process and the conditions thereof are well known in the art as illustrated by the aforementioned U.S. Pat. No. 3,527,809, U.S. Pat. No. 4,329,511 U.S. Pat. No. 4,148,830 and U.S. Pat. No. 4,247,486. Such hydroformylation processes in general involve the production of aldehydes by reaction of an olefin compound with hydrogen and carbon monoxide gas in a liquid reaction medium which contains a soluble rhodium catalyst complex with an organophosphorus ligand and solvent.

It is to be understood that the particular hydroformylation reaction conditions employed in either the primary reaction process or the secondary reaction process are not critical to the subject invention and may be varied widely and tailored to meet the individual needs of the particular reactors utilized as well as to produce the particular aldehyde product desired.

For this invention, Group VIII metals broadly, particularly, rhodium and ruthenium and especially rhodium, are employed in organometallic complexes as catalysts for the reaction of a synthesis gas (i.e., a mixture of hydrogen and carbon monoxide) with alpha-olefins to form aldehyde derivatives of the olefins which have one more carbon atom than the parent olefin. A wide range of olefinic feedstocks can be employed in such processes, including substituted olefins and especially olefins having no heteroatoms other than oxygen. While the present process improvement is broadly applicable to the hydroformylation of olefins of 2–20 carbon atoms, its most useful application are with olefins, and especially alpha-olefins of 2 to 8 carbon atoms. The process is particularly suitable for hydroformylating ethylene and propylene to propionaldehyde and n-butyraldehyde respectively. In this invention, the same catalyst complex and olefin are used for both the primary and secondary reaction processes. The catalyst is circulated continuously between the two reaction processes and the unconverted olefin in the primary reaction process is introduced into the secondary plug-flow reactor for conversion to aldehyde.

These known hydroformylation processes are carried out at superatmospheric pressure, typically under a partial pressure of about 4 to 20 atmospheres of hydrogen and carbon monoxide combined and with the molar ratio of hydrogen to carbon monoxide being about 0.5:1 to 10:1. The hydroformylation reaction temperature is normally within range of 80° C. to 150° C., preferably in the range from about 100° C. to about 120° C.

The liquid reaction medium or catalyst solution which is employed comprises, (a) the catalyst complex, (b) typically, an excess of the organic ligand employed in forming the complex over and above the mount required to complex the metallic component of the catalyst, (c) the hydroformylation reaction product along with by-products typically resulting from undesired condensation of the hydroformylation product aldehyde with itself, (d) a quantity of the olefin being hydroformylated, in an amount varying with the molecular weight of said olefin (the proportion of liquid olefin in the reaction medium usually being greater with high molecular weight olefins than with lower alkanes such as ethylene), and (e) an inert reaction solvent.

The catalyst contained in the reaction mixture can be, as known in the art, any Group VIII metal complexed with an organic ligand. The catalytic metal is complexed with hydrogen and carbon monoxide as well as with an organic ligand. While many organic ligands can be employed, those of particular significance comprise either monodentate or polydentate triorganophosphines, triorganophophites, triorganoarsines, or triorganostibines, with the phosphines and phosphites being of particular industrial importance. Simple monodentate phosphines and phosphites, as exemplified by triphenylphosphine and triphenylphosphite, are commonly employed industrially. However, polydentate ligands have advantages in that the large excesses of ligand which are often used with the monodentate ligands are not needed. For example, the phosphine-modified ferrocene-based ligands as taught in U.S. Pat. No. 4,138,420 to Unruh et al, are applicable as well as the sterically restricted bidentate phosphorus-containing ligands described in U.S. Pat. No. 4,139,565. Ligands modified by the incorporation of electronegative substutuents into the molecule also have advantages, as set forth in U.S. Pat. No. 4,152,344 to Unruh. The catalytic complex can be formed in situ in the hydroformylation reactor, or it can be preformed.

The concentration of catalyst to be maintained in the hydroformylation reaction medium is not critical to the successful employment of the present invention. Typically, however, when the catalytic metal is rhodium and when the ligand is triphenylphosphine, the liquid reaction medium will contain about 0.01 to 1.0% rhodium and up to about 20% or more triphenylphosphine by weight where suppression of iso-aldehydes is desired. In hydroformylating ethylene, the iso-aldehydes problem does not exist, and low ligand concentrations can be employed. In the absence of the added inert reaction solvent, the triphenylphosphine content in hydroformylating propylene, for example, may be as high as about 40%. Typically, the ligand concentration will not exceed about 55 weight percent.

The identity of the inert solvent which is optionally used in the reaction system as taught by the prior art is not overly critical so long as it be miscible with the catalyst system and with the reactants and reaction products, low in volatility so as to facilitate stripping reaction product and by-products from it, and, of course, either chemically inert in the hydroformylation reaction system or else forming in that system a derivative which is itself inert while still fulfilling the other named requirements. (That is, a suitable solvent could be one which might undergo hydrogenation in the reactor and then in the hydrogenated form, be inert to further reaction.) Molecular weight is not a significant factor in the reaction solvents as taught in the prior art except as it relates to volatility, relatively high molecular weight being desired, of course, to facilitate retention of the inert solvent as a heavy end while the reaction products are stripped therefrom. Thus, in the prior art as exemplified by U.S. Pat. No. 4,151,209, it is already known to employ any of a large number of inert liquids including, for example, alkyl-substituted benzenes; pyridine and alkyl-substituted pyridines; tertiary amines; high-boiling esters such as dialkyldicarboxylates and triorganophosphates as well as esters of polyols such as trimethylolpropane and pentaerythritol; ketones; alcohols such as the butanols; nitriles such as acetonitriles; and hydrocarbons including both saturated hydrocarbons such as kerosene, mineral oil, cyclohexane, naphtha, etc. and aromatics such as biphenyl. It is further emphasized in U.S. Pat. No. 4,151,209 that, in addition to the prior art solvents as just listed, the high degree of stripping taught by the patentees makes it desirable to employ solvents which are of extremely low volatility, in particular compounds or mixtures of compounds which are less volatile than the ligands used in the hydroformylation reaction many of which are themselves of very low volatility. Thus, it is taught in U.S. Pat. No. 4,151,209 that particularly useful solvents include triphenylphosphine oxide and polyglycols, e.g. polyethylene glycol and polypropylene glycol, which have molecular weights of at least about 500. The teachings of the patentees are that molecular weight of the polyalkylene solvents is important as a factor relating to volatility, with molecular weights in and of itself not otherwise being significant. Especially preferred which fit all the criteria just set forth and which are also available industrially in a wide range of molecular weights, are the polyalkylene glycols, especially, because of their ready availability, polyethylene glycol and polypropylene glycol. In this context, the term "polyalkylene glycol" refers both to polyalkylene glycols as such (that is, to polymeric alkylene glycols having a hydroxy group at each end) and also to those having one or both ends capped with an alkyoxy group such as butoxy. In addition to being readily available in a wide range of molecular weights, these materials are suitably inert and also compatible with the several components of the hydroformylation system.

As mentioned previously, it is also known to use as solvent some or all of the high-boiling aldehyde condensation products which are formed as by-products in the course of the hydroformylation reaction, as taught in U.S. Pat. No. 4,148,830 to Pruett et al. Such heavy end solvents, however, are not preferred as it is believed over prolonged periods of time such solvent may poison the catalyst and/or result in excessive foaming of the liquid reaction medium.

The present improved process is conducted in a manner similar to prior art hydroformylation process employing an added inert solvent. In the secondary reactor, catalyst solution withdrawn from the primary reactor is mixed with vapor from the primary reactor vent and additional syn gas prior to passage through the interior tubes of the plug-flow reactor. In general, the hydroformylation process of the present invention comprising a primary oxo reactor and a secondary plug-flow reactor for converting the unreacted olefin from the primary reactor to aldehyde operates as follows. In the primary reactor, mechanical agitation of the liquid contents of the hydroformylation reactor can be employed if desired, but it is simple and satisfactory to obtain adequate agitation by sparging the synthesis gas through the liquid reaction medium. In the preferred embodiment, a portion of the aldehyde product is removed in the form of a vapor from the head space of the primary reactor above the liquid level of the reaction medium such as by the syn gas which is bubbled through the reactor medium. The product vapor is condensed and directed to a gas-liquid separator whereby the liquid aldehyde product is removed from the non-condensed gas which remains. The separated vapor phase includes the unreacted syn gas and olefin as well as gaseous by-products such as alkanes, carbon dioxide, methane, nitrogen, etc. a portion of which is usually vented. The crude liquid aldehyde product can be further purified. Such type of continuous hydroformylation system is well known in the art and need not be particularly detailed herein.

A portion of the liquid catalyst solution containing the rhodium-complex catalyst, any free organophosphorus ligand, solvent, a small amount of product aldehyde and any liquid heavy end product is continuously withdrawn from the primary oxo reactor. The withdrawn portion of the liquid catalyst solution is directed to the secondary plug-flow reactor where it is mixed with the non-condensed vent gas separated from the product taken overhead the primary oxo reactor. Additional syn gas is added to the vent gas prior to mixing with the liquid catalyst solution in the secondary reactor. The mixture of liquid catalyst solution and vent gas from the primary oxo reactor and make-up syn gas is directed through the interior of elongated hollow tubes of the plug-flow reactor. Liquid catalyst solution is taken from the outlet of the plug-flow reactor. This liquid catalyst solution will contain the rhodium-complex catalyst as well as a major portion of the product aldehyde formed in the secondary reactor. The liquid catalyst solution which is removed from the secondary plug-flow reactor can all be directed to the primary oxo reactor whereby all the liquid product obtained in the process will be removed from the primary reactor.

Alternatively, the liquid catalyst solution removed from the secondary plug-flow reactor can be directed to a flasher to yield a vapor aldehyde product and a liquid catalyst solution containing rhodium-complex catalyst, free ligand and solvent. The vaporized product can be condensed and combined with product obtained from the primary reactor for further purification. The catalyst solution without substantial portions of the aldehyde product is then directed to the primary oxo reactor.

From the overhead the plug flow reactor is withdrawn a vapor containing small amounts of product aldehyde, and non-condensable gases including unreacted olefin, syn gas and by-products such as alkanes. The vapor is condensed and the liquid aldehyde product is then separated from the gases in a gas-liquid separator. The liquid aldehyde product can then be mixed with the product from the primary reactor for further purification. The amount of vent gas which remains is substantially smaller than that from the primary oxo reactor and will contain smaller amounts of unreacted olefin than previous vent streams without use of the secondary hydroformylation process.

The combined product stream from the primary reactor and secondary reactor can be fed to a product separation zone wherein a crude aldehyde product is recovered by conventional techniques, e.g. distillation. Undissolved light gases are also vented off in the product separation zone and can be returned to the primary reactor. These off gases may be merely purged, if desired, as in the case of the vent stream from the secondary reaction system.

It should be understood that the olefin starting material for the secondary reaction process can be taken from any gaseous stream which could be vented from the primary process as off-gas. While such olefin starting material for the secondary coupled process can be derived from any appropriate gas vent containing unreacted olefin and incidental by-products taken from any suitable location in the primary reaction system, it is preferred to employ the vent stream from either of the reactor head space and/or from any product separation step as the feed for the secondary coupled rhodium-catalyzed hydroformylation process. In the secondary process, the olefin-containing vented gas from the primary system is admixed with make-up syn gas and the resulting feed is introduced into the reactor of the secondary system as previously described.

Accordingly, the embodiments of this invention can be further illustrated by reference to FIG. 1 which shows a diagramatic flow sheet suitable for practicing this invention.

Referring to FIG. 1, a stainless steel reactor 10 is provided with a sparger (not shown) having holes for providing a sufficient gas flow of olefin and synthesis gas. One or more spargers may be employed depending upon the size of the reactor. In the system illustrated, propylene is converted to butyraldehyde. Feed lines 12 and 14 supply the propylene and syn gas respectively to line 15 for introduction of these gases into reactor 10. An impeller maybe employed to mix the reactor contents although such is not necessary as the sparging of the gas through the liquid catalyst solution is often sufficient to mix the reactor contents. An internal or external cooler (not shown) can be employed to help control reaction temperature. In the preferred embodiments of this invention, a vaporous product effluent from reactor 10 is removed by line 16 and passed to a condenser 18 to condense the aldehyde product from the vent gases. A gas-liquid separator 20 is used to separate the condensed crude aldehyde product from the non-condensed vent gases. Condensed aldehyde liquid is recovered from gas-liquid separator 20 via line 22 and refined as desired. Preferably, the condensed crude aldehyde product is directed from line 22 to line 24 where it is combined with crude aldehyde product obtained from the secondary reactor. The non-condensed vent gases are directed from gas-liquid separator 20 via line 28. The non-condensed vent gases contain unreacted olefin (propylene) and syn gas as well as by-product gases such as propane, methane, $CO_2$, etc.

A protion of the unreacted olefin-containing vent gas in line 28 is then introduced into a secondary coupled plug-flow reactor 30 via line 32. The remaining vent gas is recycled to primary reactor 16 via lines 26 and 70. If necessary, make-up syn gas via line 34 is mixed with the vent gas stream 32 prior to entering reactor 30. Secondary plug-flow reactor 30 is coupled to the primary oxo reactor 10 inasmuch as liquid catalyst solution is continuously withdrawn from reactor 10 via line 36 and introduced into the secondary plug-flow reactor 30 via line 37 for mixture with the combined gas stream 32 containing the olefin-containing vent gas comprising a portion of line 28 and make-up syn gas through line 34. Small amounts of unreacted olefin are also dissolved in the liquid catalyst solution from reactor 10. To insure the proper inventory of rhodium and organophosphorus ligand in the total reaction system of this invention, make-up rhodium and ligand such as triphenylphosphine can be added to line 36 via lines 38 and 40, respectively. Circulation of catalyst solution between reactors 10 and 30 allows the make-up rhodium and ligand to be uniformly dispersed.

Secondary reactor 30 is characterized as a plug-flow reactor and is designed to have the requirements known in the art to achieve plug-flow kinetics. Reactor 30 comprises a series of hollow tubes 31 held in place by tube sheets 33 and 35 and placed in a shell 39. The shell 39 includes an inlet headspace 41 wherein the liquid catalyst solution withdrawn from primary oxo reactor 10 via line 36 and introduced to reactor 30 via line 37 is mixed with the combined gas stream 32 comprising the olefin-containing vent gas via a portion of line 28 and make-up syn gas introduced into the reactor via line 34. The combined gas stream is mixed with the liquid catalyst solution by passage through sparger 42 which bubbles the gas through the liquid and provides for uniform mixing of the gas in the liquid catalyst stream. The mixture of catalyst liquid and combined gas stream passes from the inlet head space into the interior of the hollow tubes 31. Plug-flow is achieved in secondary reactor 30 by limiting the velocity of the liquid stream in the tubes to less than 0.2 feet per second, preferably 0.05 to 0.15 feet per second. Plug flow reaction kinetics are also achieved by insuring that the length to diameter ratio (L/D) of individual tubes 31 is at least 80:1, preferably 100:1 or greater, e.g. 120. Secondary plug flow reactor 30 is cooled by water circulated in the shell side of the reactor. Gas cooling can also be used. The use of a plug flow reactor 30 for the secondary reaction process is advantageous inasmuch as a reactor with plug flow kinetics can convert approximately four to five times the volume of feed that a stirred tank reactor of the same volumne can convert.

A liquid hydroformylation reaction stream is removed from the outlet head space 44 in plug flow reactor 30 via line 46. The liquid stream comprise product aldehyde (butyraldehyde), and catalyst solution comprising rhodium complex, free ligand and inert solvent if used. In the embodiment shown in the figure, the liquid stream via line 46 is introduced into flasher 48 to vaporize the product and separate the product from the catalyst liquids. The vaporized crude aldehyde product leaves flasher 48 via line 52. The flashed product vapor in line 52 is condensed in condensor 53 and the product aldehyde is separated as a liquid from the vent gases therein. Vent gases leave condenser 53 via line 57. The liquid product from condenser 53 via line 55 is combined with product obtained from reator 10 via line 24. In the head space 44 above the liquid in reactor 30 a vent stream comprising samll amounts of aldehyde product, unreacted olefin, syn gas as well as gaseous by-products is removed from reactor 30 via line 54. The vent gases leaving reactor 30 via line 54 are condensed in condenser 56. The condensed crude aldehyde product liquid is separated from the vent gases in gas-liquid separator 58. The vent gaseous stream leaves separator 58 via line 60 and is combined with vent gas removed in flasher 48 via line 57. The liquid product stream leaving separator 58 via line 62 can be combined with the condensed product from primary oxo reactor 10 via line 24 and from secondary reactor 30 via line 55 for purification such as in distillation column 64 to yield a liquid aldehyde product, i.e. buytraldehyde, leaving distillation 64 via line 66 and a gaseous stream via line 68 which can be recycled to the primary oxo reactor 10 via line 70 and will contain some propylene feed.

The liquid catalyst solution containing rhodium, organophosphorus ligand, some aldehyde product and inert solvent can be directed from flasher 48 back to primary oxo reactor 10 via line 50 and introduced into reactor 10 through nozzles 51 to maintain mixing of the liquid catalyst medium in primary reactor 10.

Alternatively, flasher 48 can be eliminated and the liquid withdrawn from secondary plug flow reactor 30 via line 46 can all be introduced into primary oxo reactor 10 in which case butyraldehyde recovery would be almost solely achieved in the primary reaction process except for buytraldehyde leaving reactor 30 via line 54.

As an alternative to the process shown in the Figure in which a gaseous aldehyde product is taken from the primary oxo reactor 10, it is also possible to withdraw product from the reactor with a liquid catalyst stream. The liquid catalyst stream can be flash distilled to separate the aldehyde product from the liquid catalyst complex, organophophorus ligand, inert solvents, heavy ends, etc. This liquid catalyst stream can be recycled back to reactor 10 or may form the liquid catalyst stream which is directed to the secondary reaction system.

It will be understood that for the purposes of this invention more than one reactor can be employed in series or in parallel in both the primary or secondary processes of this invention.

EXAMPLE

The following Example illustrates a typical oxo reaction system utilizing the secondary vent reactor of the present invention.

The primary oxo reactor is a back mixed reactor in which propylene and syn gas are sparged through the liquid catalyst solution. No further mechanical agitation is included in the reactor, although counter-current liquid circulation may promote mixing. The secondary vent reactor is designed for plug flow kinetics and is as described above in which a plurality of hollow tubes having a two inch diameter and about 20 feet long are placed inside the shell of a reactor. Coolant water circulating through the shell side of the reactor maintains the reaction temperature.

The catalyst solution which is continuously circulated throughout the system comprises 1200 ppm rhodium and 30 percent triphenylphosphine (TTP), approximately 50 weight percent UCON oil LB-625®, from Union Carbide and smaller percentages of buytraldehyde product and other by-products including heavy ends.

The reaction scheme includes the primary oxo reactor, secondary reactor, gas-liquid separators for the vapor product from the primary reactor and vent gas from the secondary reactor and a flasher to separate the product aldehyde vapor from the liquid catalyst solution leaving the secondary reactor. 10:1 ratio of normal to iso-buytraldehyde. Approximately 2% propane is formed.

The vent stream leaving the secondary gas-liquid phase separator is approximately 3,500 pounds per hour of which 500 pounds is unreacted propylene. Thus, the propylene comprises 15% of the vent stream. Prior to the present invention, in which the secondary plug flow reactor was not in line, the vent stream being purged comprised approximately 8,100 pounds per hour of which 35% or about 2,850 pounds per hour of unreacted propylene were purged.

Accordingly, by including the secondary plug flow reactor, both the vent gas and the concentration of propylene in the vent gas is reduced by more than half thus, cutting the amount of propylene purged from the system by 75–80%. Temperatures and pressures for each of the vessels are as follows:

|  | T °C. | PSIG |
|---|---|---|
| Primary oxo reactor | 120 | 310 |
| Secondary Vent Reactor | 120 | 280 |
| Primary gas-liquid separator | 49 | 305 |
| Secondary gas-liquid separator | 49 | 270 |
| Flasher | 110 | 30 |

For a system utilized to produce approximately 1 million pounds per day of butyraldehyde, the liquid catalyst solution inventory in the process is as follows: 5,000 gallons of catalyst solution in the primary oxo reactor, 3,200 gallons of catalyst solution in the secondary plug flow reactor and 800 gallons of catalyst solution being pumped through the remaining vessels and piping of the process as shown in the drawing.

The gaseous feed to the primary reactor comprises 25,600 pounds per hour propylene and 18,300 pounds per hour of syn gas having an approximate 1:1 ratio of CO and hydrogen. Vent gas entering the secondary plug flow reactor is 6,150 pounds per hour with a make-up syn gas directed to the secondary plug flow reactor of 3,150 pounds per hour.

Total propylene conversion is approximately 98% in which the product comprises a

What is claimed is:

1. In a primary rhodium-catalyzed hydroformylation process for producing aldehydes, wherein an olefin, carbon monoxide and hydrogen are reacted in the presence of a solubilized rhodium-phosphorus complex catalyst, to produce an aldehyde product, and wherein a gaseous effluent comprising unreacted olefin and any of said aldehyde product, hydrogen, carbon monoxide, alkane and inerts is vented from the process, the improvement which comprises: conducting a coupled secondary rhodium-catalyzed hydroformylation process simultaneous with said primary process, wherein said gaseous effluent from primary reactor together with make-up carbon monoxide and hydrogen is employed as the reactant feed to the secondary process and wherein said solubilized rhodium-phosphorus complex catalyst is circulated between said primary and secondary process.

2. The process of claim 1 wherein the primary rhodium-catalyzed hydroformylation process produces a product vapor, said product vapor is cooled to form a condensed crude liquid aldehyde product and a vent gas comprising said gaseous effluent.

3. The process of claim 1 wherein said secondary process is conducted in plug-flow reactor.

4. The process of claim 1 wherein said rhodium-phosphorus complex catalyst is a triorganophosphine compound.

5. The process of claim 4 wherein the triorganophosphine compound is triphenylphosphine.

6. The process of claim 1 wherein make-up olefin is not added to the coupled secondary process.

7. The process of claim 1 wherein said rhodium-phosphorus complex catalyst is solubilized in solvent.

8. The process of claim 7 wherein said solvent is inert and produced outside said hydroformylation process.

9. The process of claim 8 wherein said inert solvent is a polyalkylene glycol.

10. The process of claim 3 wherein a liquid product is taken from said plug-flow reactor and said liquid product flashed to form a product aldehyde vapor and a non-volatile catalyst solution comprising solubilized rhodium-phosphorus complex catalyst, said non-volatile catalyst solution being circulated to said primary hydroformylation process.

11. The process of claim 3 wherein a liquid product is taken from said plug-flow reactor, said liquid product comprising solubilized rhodium-phosphorus complex catalyst and aldehyde product, all of said liquid product being directed to said primary hydroformylation process.

12. The process of claim 1 wherein said solubilized rhodium-phosphorus complex catalyst is continually circulated between said primary and secondary hydroformylation processes.

13. The process of claim 1 wherein said rhodium-phosphorus complex catalyst is solubilized in a liquid catalyst solution containing an inert solvent, said rhodium concentration in said catalyst solution comprising 0.01 to 10 weight percent rhodium (calculated as Rh metal).

14. The process of claim 13 wherein said catalyst solution comprises up to 55 weight percent of the phosphorus ligand.

15. The process of claim 1 in which said olefin has from 2–8 carbon atoms.

16. The process of claim 15 wherein said olefin is propylene.

17. The process of claim 1 wherein the hydroformylation reaction in the primary and secondary process is conducted at reaction temperature from about 80° C. to 150° C.

18. The process of claim 17 wherein the hydroformylation reaction temperature in primary and secondary process is in the range from about 100° C. to 120° C.

19. The process of claim 9 wherein said inert solvent is polyethylene glycol or polypropylene glycol having a molecular weight of at least 500.

20. The process of claim 8 wherein said polyalkylene glycol inert solvent is end-capped with an alkoxy group.

* * * * *